United States Patent [19]

Jansen

[11] Patent Number: 5,365,943
[45] Date of Patent: Nov. 22, 1994

[54] ANATOMICALLY MATCHED STEERABLE PTCA GUIDEWIRE

[75] Inventor: Lex P. Jansen, Londonberry, N.H.

[73] Assignee: C. R. Bard, Inc., Murray Hill, N.J.

[21] Appl. No.: 30,808

[22] Filed: Mar. 12, 1993

[51] Int. Cl.⁵ ............................................. A61B 5/00
[52] U.S. Cl. ................................................... 128/772
[58] Field of Search ................ 128/657, 772; 604/95, 604/280, 283

[56] References Cited

U.S. PATENT DOCUMENTS

| | | | |
|---|---|---|---|
| 4,545,390 | 10/1985 | Leary | 128/772 |
| 4,619,274 | 10/1986 | Morrison | 128/772 |
| 4,682,607 | 7/1987 | Vaillancourt et al. | 128/772 |
| 4,799,495 | 1/1989 | Hawkins et al. | 128/754 |
| 4,830,023 | 5/1989 | de Toledo et al. | 128/772 |
| 4,925,445 | 5/1990 | Sakamoto et al. | 604/95 |
| 4,934,380 | 6/1990 | de Toledo | 128/657 |
| 4,935,068 | 6/1990 | Duerig | 148/11.5 C |
| 4,944,727 | 7/1990 | McCoy | 604/95 |
| 4,984,581 | 1/1991 | Stice | 128/772 |
| 4,991,602 | 2/1991 | Amplatz et al. | 128/772 |
| 5,007,434 | 4/1991 | Doyle et al. | 128/772 |
| 5,025,799 | 6/1991 | Wilson | 128/772 |
| 5,055,101 | 10/1991 | McCoy | 604/95 |
| 5,067,489 | 11/1991 | Lind | 128/772 |
| 5,069,226 | 12/1991 | Yamauchi et al. | 128/772 |
| 5,098,412 | 3/1992 | Shiu | 128/772 |
| 5,111,829 | 5/1992 | Alvarez de Toledo | 128/772 |
| 5,120,308 | 6/1992 | Hess | 604/95 |
| 5,129,890 | 7/1992 | Bates et al. | 128/657 |
| 5,135,503 | 8/1992 | Abrams | 604/164 |
| 5,143,085 | 9/1992 | Wilson | 128/772 |
| 5,171,383 | 12/1992 | Sagaye et al. | 128/772 |

FOREIGN PATENT DOCUMENTS

| | | | |
|---|---|---|---|
| 0306010 | 3/1989 | European Pat. Off. | 128/772 |
| 0491349 | 6/1992 | European Pat. Off. | 128/772 |

OTHER PUBLICATIONS

"Selective Coronary Arteriography", Radiology pp. 815-824 Nov. 1967.

*Primary Examiner*—Max Hindenburg
*Attorney, Agent, or Firm*—Wolf, Greenfield & Sacks

[57] ABSTRACT

A small diameter steerable guidewire adapted for use in percutaneous transluminal coronary angioplasty has three segments, each adapted to reside in a separate region of the arterial and coronary anatomy during angioplasty. The proximal segment is adapted to reside proximally of the aortic arch and has high torsional rigidity for enhanced pushability and rotational transmission. An intermediate segment is adapted to reside in the region of the aortic arch and is more flexible than the proximal section while maintaining a high degree of rotation transmission. The distal segment is more flexible than the intermediate segment and is dimensioned to reside from a region proximally of the primary curve of the guidewire to and into the coronary arteries.

26 Claims, 3 Drawing Sheets

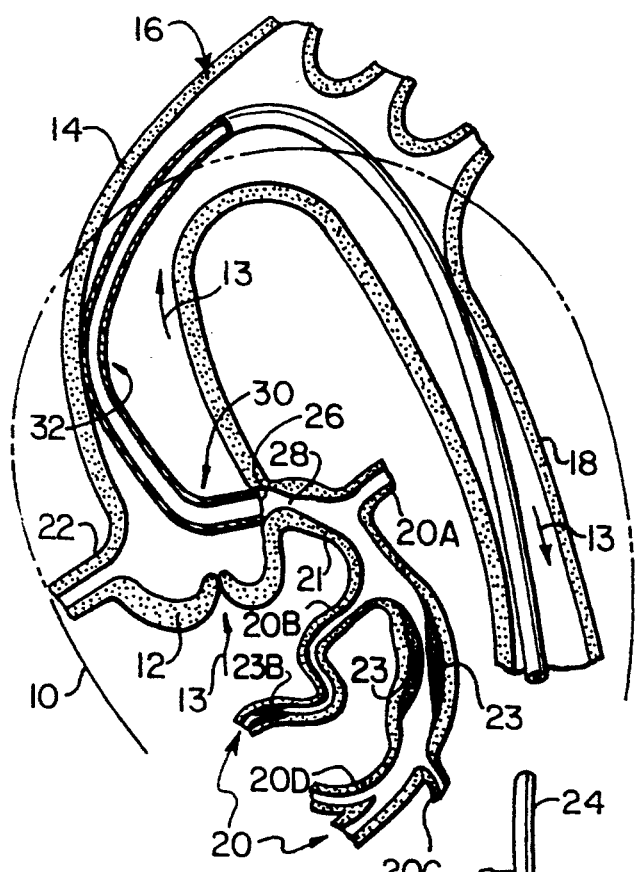
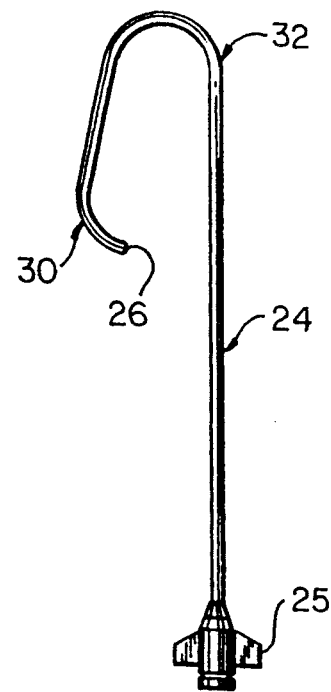
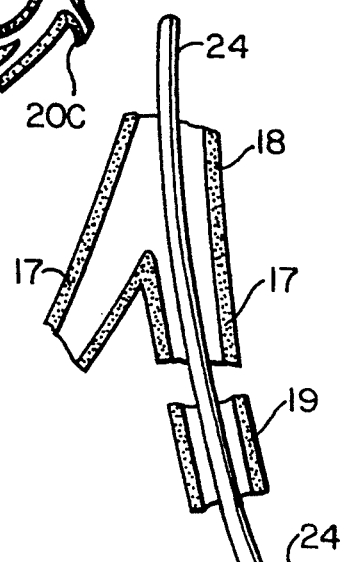
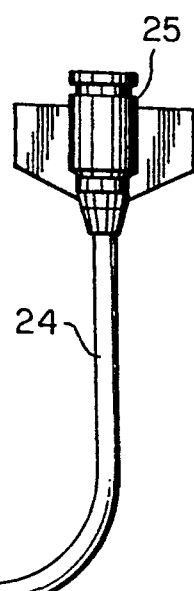
Fig.1
Fig.1A

ANATOMICALLY MATCHED STEERABLE PTCA GUIDEWIRE

FIELD OF THE INVENTION

This invention relates to small diameter steerable guidewires used in percutaneous transluminal coronary angioplasty (PTCA).

BACKGROUND OF THE INVENTION

The invention concerns improvements in guidewires used with balloon dilatation catheters and, particularly, with the over-the-wire type of such catheters used in PTCA, in which a stenosed region of a coronary artery is dilated to increase the blood flow through that artery. The PTCA procedure typically involves advancement of a guide catheter through a percutaneous puncture in the femoral artery to place the distal end of the guide catheter at the entrance (ostium) to one of the two (right or left) main coronary arteries. With the guide catheter properly positioned, a balloon dilatation catheter then is passed through the guide catheter to the ostium of and then into, the coronary arteries. The balloon dilatation catheter typically is used in conjunction with a small diameter steerable guidewire that can be manipulated into the selected arterial branch and through the stenosis that is to be dilated. After the guidewire has been manipulated and navigated into place, the balloon catheter is advanced over and along the guidewire, with the balloon in a deflated state to place the balloon within the stenosis. The balloon then is inflated to dilate the stenosed region of the artery.

Numerous difficulties are presented in the design of a small diameter steerable guidewire for use in PTCA. The difficulties may be appreciated from an understanding of the human arterial anatomy from the usual point of entry, the femoral artery in the groin region, to and including the coronary arteries. The portion of that arterial anatomy is illustrated, in fragmented, somewhat diagrammatic fashion, in FIG. 1. The arterial system carries blood from the heart, indicated as to general region in phantom at 10 through the aortic valve 12 of the heart 10 in a direction indicated by the arrows 13. The arterial system leading from the aortic valve 12 includes, in a downstream direction, the ascending portion 14 of the aorta, the aortic arch, indicated generally at 16 and the remaining (descending) portion 18 of the aorta. Numerous arteries branch off the aorta to carry blood to the internal organs of the body as well as the limbs and extremities, including the iliac arteries 17 and femoral arteries 19 that direct blood to the legs. The coronary artery system (suggested schematically and in part at 20) through which oxygenated blood is directed back to the heart tissue itself includes two main arteries, a left main coronary artery 21 and a right main coronary artery 22, both of which branch off the ascending portion 14 of the aorta close to the aortic valve 12. Each of the left and right coronary arteries 21, 22 leads to a system of numerous branch arteries, some of which are suggested schematically at 20A, 20B, 20C, 20D, that spread out over the wall of the heart muscle thereby serving to distribute oxygenated blood to the entire heart muscle. The object of the PTCA procedure is to treat the portion of an artery that has developed a stenosis, for example, as suggested at 23 which obstructs blood flow through that portion of the artery. The PTCA procedure dilates the stenosis 23 to enlarge the flow area and improve the flow of blood to those portions of the heart tissue served by the stenosed artery.

The PTCA procedure involves initial placement of a comparatively large diameter guide catheter 24 (of the order of about 6 French (0.078" outer diameter) to about 9 French (0.117" outer diameter) through a percutaneous puncture (not shown) in the femoral artery 19. The guide catheter 24 has a specially formed distal end that facilitates engagement of the tip 26 of the guide catheter with the entrance (ostium) 28 to one or the other of the main coronary arteries 21, 22. FIG. 1A illustrates a "Judkins-left" type of guide catheter adapted to intubate the ostium 28 of the left main coronary artery 21. The Judkins-left guide catheter has two principal pre-formed curves at its distal region including a primary curve 30 located approximately one-half to one centimeter from the distal tip 26 of the catheter and a secondary curve 32 located about three to six centimeters from the tip 26. The portion of the guide catheter proximally of the secondary curve 32 is essentially straight all the way to the fitting 25 at the proximal end of the catheter. As illustrated in FIG. 1, when the catheter is deployed in the patient, the secondary curve 32 bears against the wall of the aorta generally opposite the ostium in order to help stabilize the deployed position of the guide catheter. The primary curve serves to direct the tip 26 substantially at the ostium to the left main coronary artery. A normally straight portion of the guide catheter 24 disposed proximally of the secondary curve 32 is sufficiently flexible so that it can be bent through the relatively large radius bend of the region of the aortic arch 16. In this regard, it may be noted that guide catheters typically are formed to include polymeric materials that tend to soften somewhat and become more flexible when exposed to body temperature, thereby facilitating bending of the distal region of the guide catheter to conform to the aortic anatomy in the region of the heart.

As suggested in FIGS. 1 and 1A, the primary and secondary curves 30, 32 of the guide catheter 24, when deployed as well as when relaxed, define a sharper bend than that through which the more proximal portion of the guide catheter assumes when it passes through the aortic arch 16. Typically, the primary and secondary curves 30, 32 may have a radius of the order of one-half to one inch as compared to the radius of the order of one and one-half to two inches for the curve that may be assumed through the aortic arch. The guide catheter 24, once placed, defines a path through and along which an angioplasty catheter (which typically is far more flexible than the guide catheter and about 0.040 inches diameter or less) and guidewire can be advanced easily and quickly to the entrance 28 of the coronary artery. The guide catheter typically is placed in a procedure well-known to those familiar with the art.

In a typical procedure, a small diameter (less than about 0.020 inches and preferably of the order of 0.018 inches or less) steerable guidewire, indicated generally at 34 (FIG. 2) is preloaded into the receptive guidewire lumen (not shown) in the balloon angioplasty catheter, indicated generally at 36. The angioplasty catheter 36 and guidewire 34 are advanced together through the previously placed guide catheter 24 to the ostium 28. Then, while holding the balloon catheter 36 in place within the guide catheter 24, the guidewire is advanced through the balloon catheter into the coronary arteries. The guidewire is manipulated from its proximal end 35 by the physician while the patient is under fluoroscopy so that the distal end of the guidewire can be observed fluoroscopically. The physician, by combined rotational and longitudinal movements of the guidewire 34, can steer the guidewire 34 through the branches of the coronary arterial tree so that the distal end 37 of the guidewire passes through the stenosis 23. Once so positioned the guidewire 34 is held stationary by the physician or an assistant and the balloon catheter 36 then is advanced over and along the guidewire 34, thereby guiding the balloon 40 of the catheter 36 directly to the stenosis 23. With the balloon in place, it then is inflated through an inflation lumen 42, typically with a liquid under high pressure to forcibly dilate the stenosis. It should be understood that for ease of illustration, the stenosis 23 in FIGS. 1 and 2 has been placed in a location in the arterial tree that is relatively free of complex tortuousities and is relatively close to the coronary ostium. It will be appreciated that in order for the guidewire to effectively serve its function of guiding the balloon catheter to the stenosis, the guidewire should be capable of being steered and manipulated into any of the arterial branches such as suggested schematically at 20A–20D as well as other branches located at the most distal portions of the coronary arterial tree. Frequently the stenosis will be located well within a highly tortuous arterial branch of the coronary anatomy such as suggested at 23B in branch artery 20B (FIGS. 1 and 2). In order to reach and treat a stenosis so located, it will be appreciated that the balloon catheter and the guidewire must be steered and advanced through the tortuous anatomy along a path suggested in phantom at 34B in FIG. 2.

In order for the guidewire to perform its function effectively, it should have a number of characteristics. The guidewire should have adequate longitudinal flexibility to enable it to conform to the various curves of the patient's arteries including the frequently highly tortuous configuration of the coronary arteries. It should have adequate column strength so that it can be pushed, as it is advanced through the arteries, without buckling. In order that the guidewire may be steered controllably, it should be sufficiently torsionally rigid to be able to transmit controllably to its distal end substantially all of the rotation applied at the proximal end. The distal tip of the guidewire should be soft and flexible to reduce the risk of injury to the delicate inner lining of the artery. The guidewire also should be kink resistant. Kinking (permanent deformation) in the guidewire typically results in aberrant, uncontrolled whipping movement at the distal tip of the guidewire rather than the desirable controlled transmission of rotation. The guidewire also desirably is highly radiopaque at its distal tip in order that its movement and position may be readily observed under fluoroscopy. Also important among the characteristics of a guidewire is that it have a good tactile response in order that the physician may feel, at the proximal end of the guidewire, events occurring at the distal end.

Since the development of the first small diameter steerable guidewire (Leary U.S. Pat. No. 4,545,390) continued development of small diameter steerable guidewires has involved trade-offs and compromises among the foregoing desirable characteristics. Among these has been the development of guidewires formed from a pseudo-elastic material, such as a nitinol alloy. The pseudo-elastic characteristic of the material provides for excellent kink resistance and a desirably soft, flexible distal tip. Typical of such guidewires are those described in U.S. Pat. No. 4,925,445 (Sakamoto). The advantages of such pseudo-elastic guidewires have been achieved, however, at the expense of other desirable characteristics, particularly in small diameter guidewires of the type now commonly used in PTCA, of the order of 0.014 inches to as small as 0.010 inches diameter. Although the performance of pseudo-elastic guidewires may be less problematic in larger sizes, the performance may become marginal when the diameter is as small as 0.014" and poor in smaller sizes. Performance becomes marginal to poor, particularly with respect to the column strength of the guidewire and its ability to be pushed without buckling. Similarly, pseudo-elastic guidewires of the order of 0.014 inch diameter and smaller, adapted for use in PTCA tend to display marginal to poor steerability characteristics. These disadvantages also compromise the tactile response of the wire.

It would be desirable to provide a small diameter steerable guidewire in which the foregoing desirable characteristics are maximized, with a minimum amount of compromise of one characteristic for another. It is a general object of the invention to provide such a guidewire.

SUMMARY OF THE INVENTION

The invention is incorporated in a small diameter steerable guidewire that has three principal sections, each having a different degree of torsional rigidity and longitudinal stiffness (flexiblity). Each of the three sections is anatomically matched and is adapted to maximize those characteristics of the guidewire that are desirable in the corresponding three distinct sections of the arterial and coronary vasculature when the guidewire is in its normal range of positions in that vasculature. Thus, for the relatively straight portion of the vasculature extending from the femoral puncture up to a location just short of the aortic arch, the guidewire is constructed to have a shaft that is quite stiff and torsionally rigid. An intermediate section of the guidewire that is intended to extend through and over the aortic arch (up to just proximal of the secondary curve 32), has a shaft constructed to provide a combination of maximum rotational transmission with sufficient flexibility to pass through the aortic arch but without adversely affecting the other desirable characteristics of the guidewire (e.g., torsional or translational transmission, etc.). The third, distal section of the guidewire includes a core wire that is contained within a helical coil. The only section that passes through the relatively short radius curves 30, 32 of the guide catheter and is actually inserted into the coronary arteries is the distal section which is constructed to have greater flexibility while maintaining the ability to adequately transmit rotation to the distal tip. The distal section of the core wire and, preferably, the intermediate shaft sections may be formed from a pseudo-elastic alloy, such as nitinol, that is essentially non-kinking and is highly flexible thereby minimizing the risk of trauma to the artery by the guidewire. A tip forming wire, formed from a malleable material may be incorporated into the tip so that the distal tip may be bent slightly to facilitate steering through the branches of the coronary arterial tree.

Thus, each of the three sections of the guidewire is adapted to provide combinations of maximal desirable characteristics such as torque transmission and pushability while providing the requisite degree of longitudinal flexibility to accommodate the degree of the anatomical curvature with substantially reduced risk of trauma to the artery.

It is among the general objects of the invention to provide a small diameter, anatomically matched, PTCA steerable guidewire having three principal sections, each adapted to maximize the performance characteristics in three distinct portions of a patient's arterial and coronary vasculature.

Another object of the invention is to provide a guidewire of the type described having a stiff proximal section, an intermediate section adapted to accommodate the aortic arch but without substantially compromising the torque transmission capabilities of the guidewire and a distal highly flexible, kink-free, yet torsionally transmissive section.

DESCRIPTION OF THE DRAWINGS

The foregoing and other objects and advantages of the invention will be appreciated more fully from the following further description thereof, with reference to the accompanying drawings wherein:

FIG. 1 is a diagrammatic, not-to-scale, fragmented and sectional illustration of the human arterial anatomy from a portion of the femoral artery to the region of the heart and with a guide catheter in place;

FIG. 1A is a fragmented illustration of a Judkins-left type of guide catheter showing the configuration of its distal end before the catheter is placed in the patient;

DESCRIPTION OF THE PREFERRED EMBODIMENT

Figure 2:
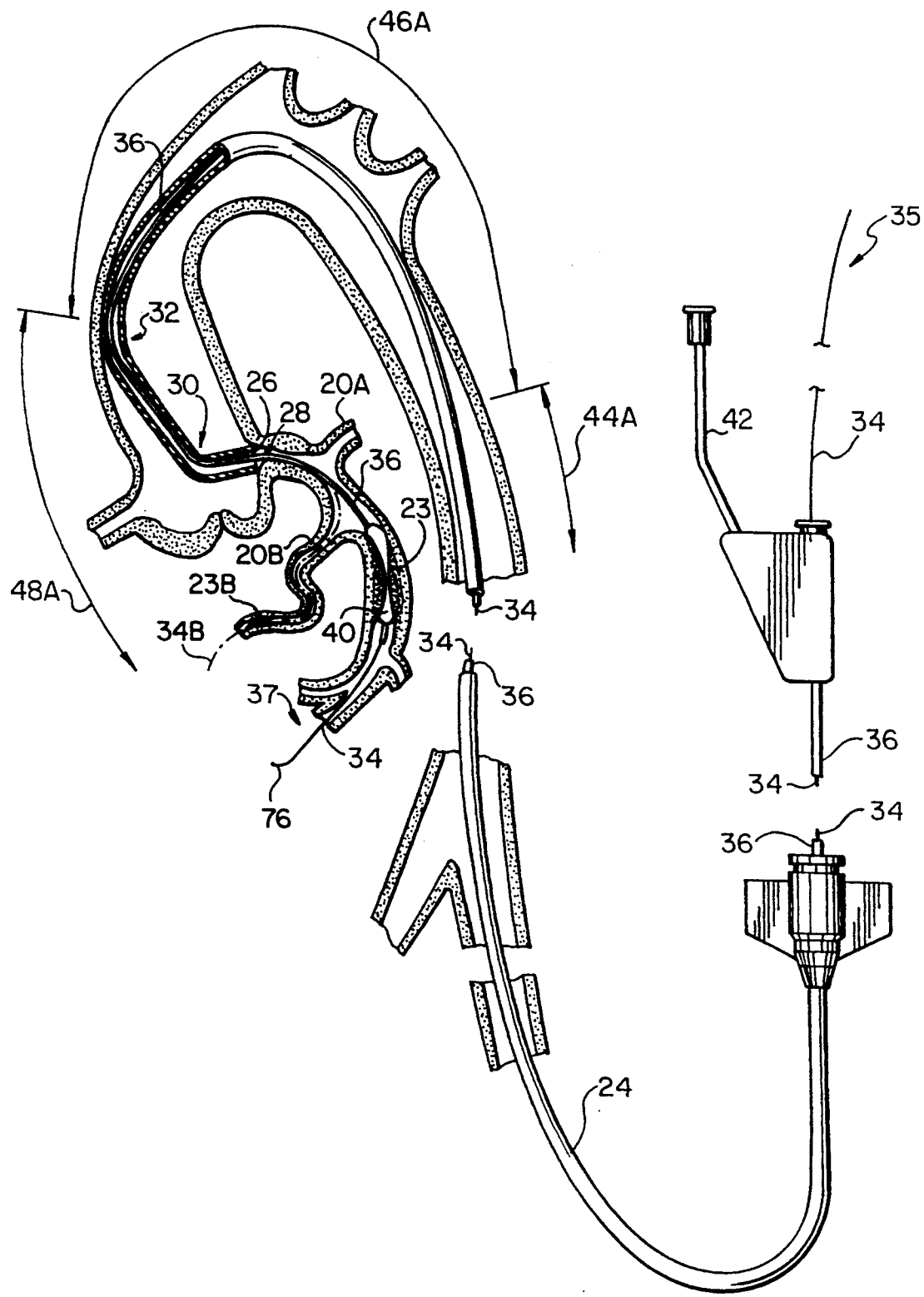
FIG. 2 is an illustration similar to FIG. 1 illustrating further the PTCA catheter and small diameter steerable guidewire positioned through the balloon catheter and with the balloon of the catheter in a stenosis in a coronary artery.
Figure 3:
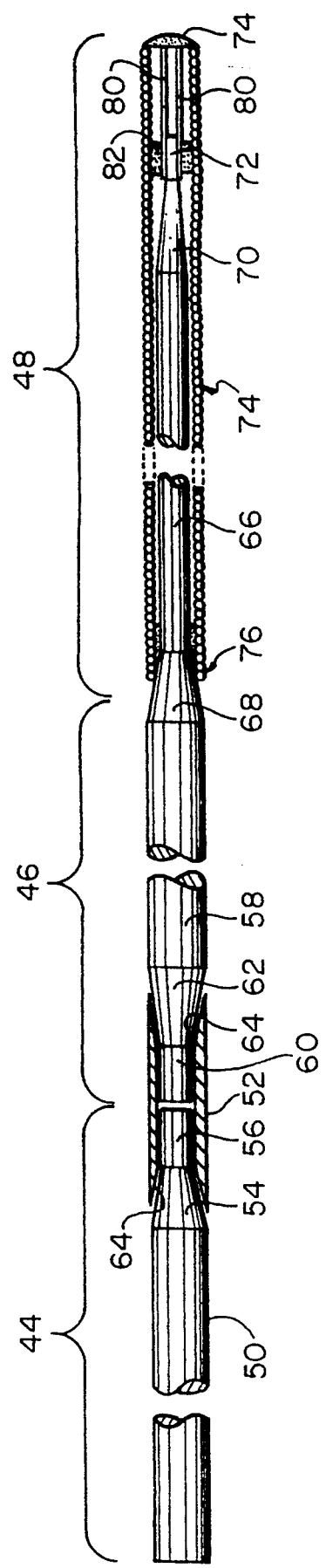
FIG. 3 is a fragmented sectional illustration of the guidewire.

The guidewire 34 may be considered as having three principal sections including a proximal section 44, an intermediate or aortic arch section 46 and a distal section 48 as suggested in FIG. 3 (fragmented and not to scale). The lengths of the principal sections 44, 46, 48 are selected specifically so that those sections will operate, respectively, in three corresponding sections of the arterial and coronary anatomy. As suggested in FIG. 2, the proximal section 44 of the guidewire is intended to operate in the femoral, iliac and aortic portion suggested generally by the arrow 48A. The intermediate (aortic arch) section 46 is intended to operate in the region of the aortic arch indicated generally by the arrow 46A of FIG. 2. The distal section 48 is intended to operate substantially in the region suggested generally by the arrow 48A in FIG. 2. It should be understood, that the optium results using the invention is achieved when the guidewire is operated in those regions. It should be understood, however, that in some circumstances, a part of the distal section of the guidewire may be withdrawn somewhat more into the aortic arch than suggested by the juncture of the regions 46A, 48A. Although performance of the guidewire would be compromised somewhat, it is believed that the guidewire still would provide improved performance as compared with prior art guidewires. In the following description, the ranges of lengths for the sections of the guidewire are intended to reflect such possible extensions of the intended optimal operating range.

The overall length of the guidewire may be of the order of 175 centimeters for a guidewire intended to be inserted through a puncture site in the femoral artery. The distal section 48 of the guidewire in the illustrative embodiment is approximately twenty-three centimeters long. The distal section 48 could have a length, if desired, as short as about 15 centimeters or as long as about thirty centimeters. The intermediate section preferably is approximately 15 centimeters long although the length of the intermediate section could range between about 12 to about 18 centimeters. The proximal section may be of the order of 140 centimeters long but may be varied somewhat, depending on the lengths of the distal and intermediate sections in order to maintain the overall length of the guidewire at about 175 centimeters. It should be understood, however, that the foregoing lengths of the respective segments are illustrative of the preferred construction for the illustrative embodiment in the context of a Judkins-left guide catheter and that the dimensions are not intended to be exact, it being understood that the length of the sections may be varied somewhat within a range, such as those suggested above, that still maintains the sections in their respective operating regions 44A, 46A, 48A when the device is in use. It also should be understood that the Judkins-left type of guide catheter is but one of numerous types having a considerable variety of curves at the distal end that will be disposed distally of the aortic arch when the catheter is deployed. Typically, such curves have similarly short radii.

Although the guidewire may be formed in various diameters, guidewires used in PTCA commonly have diameters of the order of 0.010 inches to 0.018 inches. In the description of the preferred embodiment, the diameters of the various portions of the guidewire are given with respect to a guidewire having an outer diameter of 0.010 inches.

The proximal section of the guidewire includes a cylindrical wire shaft 50. When the guidewire is deployed in the patient, the shaft 50 will be disposed in the region 44A, including the femoral and iliac arteries and the relatively straight portion of the aorta. The proximal shaft 50, therefore, need not and should not have a high degree of longitudinal flexibility. It is important that the proximal shaft 50 has high rotational transmission capability as well as high column strength to facilitate the "pushability" of the guidewire. The proximal shaft 50, therefore, is formed from a material that, taken in conjunction with the dimensions of the proximal shaft 50, will exhibit maximal rotational transmission and column strength. For a guidewire having a proximal shaft diameter of the order of 0.010 inches, the material should be no less stiff than stainless steel (modulus of elasticity of the order of 30,000,000 p.s.i.) although other, stiffer materials are preferred, such as an alloy of tungsten and rhenium. An alloy of 97% tungsten and 3% rhenium is commercially available and has been found to be satisfactory. Such tungsten-rhenium alloy is substantially stiffer than stainless steel, having a modulus of elasticity of the order of 55,000,000 p.s.i. This results in a substantially improved tactile response.

It should be noted that the proximal shaft 50 may be subjected to some large radius bending in the region of entry into the femoral artery. Typically, access to the femoral artery involves placement of a short tubular catheter introducer that serves an entry guide for all the devices (including the guide catheter) into the femoral artery. The introducer is inserted percutaneously into the femoral artery at somewhat of an angle to the femoral artery. Consequently, the region of the introducer defines somewhat of a bend. The bend, however, is a relatively large radius, for example, of the order of four inches, and does not have a materially adverse effect on the functioning of the stiff proximal section 50 of the guidewire. However, the guidewire may, if desired, be modified to include an additional short, more flexible segment (e.g., pseudo-elastic) in that portion of the proximal shaft that would correspond to that region. The ends of such more flexible segment may be attached to the adjacent ends of the stiff proximal shaft 50 by a connector tube such as that described below.

The guidewire may be coated along its length with a suitable material such as a biocompatible silicone based lubricant to reduce friction between the guidewire and the catheter. A silicone coating available from Dow Corning under the trade designation MDX4-4159 is suitable. Alternately, hydrophilic coatings may be suitable or, possibly, even more effective in reducing friction.

The distal end of the proximal shaft 50 is reduced in diameter so that it can be inserted into a connector tube 52. The distal end of the proximal shaft 50 thus includes a tapered segment 54 and a barrel (constant diameter) segment 56. The barrel segment may have a diameter of the order of 0.0055 inches and a length of about 1.5 to 2 centimeters. The tapered segment 54 may be of the order of 1 to 1.5 centimeters in length. It should be understood that other taper and barrel lengths may be employed, the foregoing intended merely to be illustrative.

The intermediate section 46 includes an intermediate shaft 58 that has a proximal end of reduced diameter essentially identical to that at the distal end of the proximal shaft 50. Thus, the intermediate shaft 58 includes a proximal barrel section 60 and a connecting tapered segment 62. The distal end of the proximal shaft 50 and the proximal end of the intermediate shaft 58 are connected by the connector tube 52. The connector tube 52 may be in the range of about two to four inches long, may be formed from stainless steel hypodermic tubing and, for the illustrative embodiment, may have an inner diameter of 0.006–0.007 inches and an outer diameter of the order of 0.010 inches. The ends of the inner lumen of the connector tube 52 are beveled as indicated at 64 to correspond to the angle of the tapered portions 54, 62 of the shafts 50, 58, respectively. As described in further detail below, the intermediate shaft 58 preferably is formed from a nickel titanium (nitinol) pseudo-elastic alloy that has significantly different melting properties than those of a tungsten rhenium alloy of the proximal shaft 50 such that the two sections are not readily joinable by conventional welding. Therefore, the junction between the shafts 50, 58 and the connector tube 52 is secured by an appropriate adhesive. Suitable adhesives may include cyanoacrylate (Locktire No. 493) or an inaerobic adhesive (Locktite No. 290). Possibly suitable epoxies may be used.

The intermediate shaft 58 and distal core wire 66 may be formed from a single wire of the nitinol alloy. The wire may be formed to the configuration of varying narrow and tapered segments by centerless grinding. Such nitinol wires may be obtained, for example, from Fort Wayne Metals Company, Fort Wayne, Ind. Nitinol alloy wires may be centerless ground, for example, by Microguide, Inc., Tehachapi, Calif.

The intermediate shaft 58 may have a diameter corresponding to the full diameter of the proximal shaft 50 and may include a constant diameter barrel segment of the order of 11.5 centimeters long and 0.010 inches diameter. The intermediate shaft 58 makes a transition to the core wire barrel portion 66 by a tapered strain relief segment 68 of the order of 3.5 centimeters in length. The core wire segment 66 has a diameter in the range of about 0.005 to 0.007 inches along its barrel segment. Distally of the barrel portion of the core wire 66 is a tapered segment 70 that merges into a tip barrel segment 72 about 1.4 centimeters long and 0.0017–0.0020 inches in diameter. The tapered segment 70 may be between about 2 to 9 centimeters long, the length of the core wire barrel portion 66 being selected to be complementary to maintain the overall length of the distal segment 48 within the range described.

The distal core wire 66 is surrounded by a helical coil 74 that is attached at its proximal end 76 to the region of the taper 68 and terminates at its distal end at a tip bead 78. The proximal end of the coil 74, which may be formed from stainless steel, is attached to the taper 68 by adhesive such as the adhesives discussed above in connection with the connector tube 52. Preferably, several turns of the coil 74 at the proximal end 76 of the coil are separated slightly to enable the adhesive to work into and among those turns to effect a secure bond with the nitinol wire.

One or more forming wires 80 made from stainless steel or other metal sufficiently malleable to be capable of retaining a bend may connect the tip barrel 72 with the bead 78. The forming wires 80 may be attached to the distal tip of the core wire by an adhesive as discussed above. The distal end of the forming wire arrangement is attached to the tip bead by a weld. Exemplary of preferred forming wires are described, for example, in U.S. patent application of William A. Berthiume filed Feb. 9, 1993 and entitled "Guidewire with Round Forming Wire" to which reference is made, the disclosure of which is incorporated herein by reference in its entirety. The forming wires enable a slight bend, suggested at 76 in FIG. 2 to be put in the tip of the wire to enhance the directional capability of the guidewire as the guidewire is rotated. The forming wire is attached to the distal tip 72 of the core wire and to the coil at an adhesive joint 82. The adhesive may be the same as that described above in connection with the attachment of the nitinol to the stainless steel connector 52. Additionally, it should be noted that the major portion of the length of the guidewire is formed from the very high modulus, torsionally rigid material along the length of the proximal section. Thus, whatever reduction in ability to transmit rotation might result from the use of a lower modulus material, such as nitinol, is considered to be more than made up by the substantially improved performance resulting from the proximal segment.

The forming wires are approximately 5 centimeters long. Alternately the nitinol tip segment 72 could be extended to the tip bead. In this alternative embodiment, the distal end of the nitinol tip barrel may be attached to the tip bead with an epoxy adhesive. Notwithstanding its pseudo-elastic characteristic, the nitinol material can be caused to exceed its yield stress and can be deformed sufficiently to form a slight bend in its distal tip. A permanent bend may be formed by bending the nitinol tip about an extremely small diameter pin, of the order of 0.020 inches in diameter.

The helical coil 74 may incorporate any one of a number of constructions for such coils as are known and familiar with those skilled in the art. The coil 74 should have a high degree of longitudinal flexibility and preferably should have at least a portion constructed to present a good radiopaque image under fluoroscopy. For example, the coil, which preferably is formed from wire of the order of 0.0015 to 0.0030 inches in diameter, may be formed from stainless steel and may be plated in whole or in part with a radiopaque material such as gold. Alternately, the coil may be formed in whole or in part from wire that is itself highly radiopaque, such as platinum tungsten alloy, as described in U.S. Pat. No. 4,545,390. Alternately, coil segments formed from materials having different degrees of radiopacity may be employed, for example, by attaching to the distal end of a stainless steel coil a tip coil formed from a highly radiopaque material. The outer diameter of the coil in the illustrative embodiment is 0.010 inches corresponding to the nominal diameter of the guidewire. A distal tip segment of the coil 74 may extend for several centimeters, or less, beyond the distal tip of the tip segment 72.

In accordance with the invention, the characteristics of the materials from which the components of the guidewire are formed coupled with the geometry and diameters of the several sections of the guidewire are believed to provide substantially improved performance. As described above, the proximal segment 44 is intended to reside in the femoral and iliac arteries and in the straight portion of the aorta. Because it is unnecessary for the proximal section to be bent to any significant degree, its torsional and column strength characteristics can be maximized. The selection, in the most preferred embodiment, of a material having a high modulus of elasticity, such as the tungsten rhenium alloy described, provides this characteristic of the wire.

The intermediate section 46 of the guidewire is designed to be more flexible so that it can pass through the aortic arch (which may have a typical radius of approximately 1.5 to two inches) without risk of becoming kinked and without significantly compromising the ability of the wire to controllably transmit rotation or its ability to be pushed while advancing the guidewire. Commercially available nickel-titanium alloy, approximately 56% nickel (by weight) and 44% titanium appears to be quite satisfactory. The nitinol alloy has a considerably lower modulus of elasticity (of the order of 7,000,000 p.s.i.) than the proximal shaft 50.

The materials for the section of the guidewire should be selected so that, coupled with the dimensions of the guidewire, the bending stress to which the various portions of the guidewire will be subjected when used to perform PTCA will not vary excessively along the length of the guidewire. It is desired that the bending stresses that are developed along the length of the guidewire as the guidewire is placed within the curved, often tortuous, arterial anatomy be maintained at reduced levels. Reduced levels of bending stress result in a reduced level in the force at which the guidewire bears against the inner surface of the catheter guidewire lumen, consequently reducing the frictional drag that is developed between the two. Increased levels of frictional drag may affect the performance of the guidewire and the tactile response sensed by the physician. Conversely, lowered friction can be expected to improve performance.

It should be understood that although a pseudo-elastic material is preferred for the intermediate section 46, it may be possible to use another material for the intermediate section. For example, stainless steel or other material having a modulus of elasticity between that of the distal section 48 and proximal section 44 may function adequately in the region of the aortic arch.

The pseudo-elastic characteristic of the alloy from which the intermediate shaft 58 (and core wire 66) are formed assures that in those portions of the guidewire that will be subjected to curves and bends, the guidewire will be able to assume those curves and bends without risk of permanent deformation or kinking. Although the nitinol alloy, might be expected to display reduced torque transmission because of its lower modulus of elasticity, the pseudo-elastic nature of the alloy enables the wire in the region 46A of the aortic arch to maintain a maximum diameter (0.010 inches in the illustrative embodiment) through substantially the entire length of the aortic arch. By maintaining the intermediate shaft 58 at the maximum diameter (i.e. the same diameter as the proximal shaft 50) the ability to transmit controllably rotation through the approximately 180° bend of the aortic arch is not excessively compromised. Additionally, it should be noted that the major portion of the length of the guidewire is formed from the very high modulus, torsionally rigid material along the length of the proximal section. Thus, whatever reduction in ability to transmit rotation might result from the use of a lower modulus material, such as nitinol, is considered to be more than made up by the substantially improved performance resulting from the proximal segment.

The distal section 48 of the guidewire is configured so that it will be exposed to the sharper radius bends that exist beginning with the secondary and primary curves 32, 30 of the guide catheter and then the various curves that can be expected to be encountered in the coronary arteries, some of which may be extremely tortuous (e.g., as small as ¼ inch radius). In order that the distal section 48 be sufficiently flexible to negotiate the relatively sharp curves and tortuousities of the curves of the guide catheter that are distal of the aortic arch and those of the coronary arteries without adversely affecting the torsional control of the wire, the core wire 66 is reduced somewhat in diameter, as discussed above. The distal section 48, however, is relatively short in relation to the overall length of the guidewire. Consequently, the degree to which the torsional characteristic of the guidewire, as a whole, are compromised as a result of the somewhat reduced diameter of the core wire 66 is minimal.

The lengths of the guidewire sections, particularly the distal section 48 and intermediate section 46 are significant aspects of the invention. The length of the distal section 48, including the core wire 66 and the extension of the coil beyond the tip segment 72 need not be more than approximately twenty-three centimeters. That is long enough so that even if the guidewire must be advanced to the most distal portion of the longest coronary artery (typically the left anterior descending artery), the juncture (the region of the taper 68) between the intermediate shaft 58 and core wire 66 will remain well within the guide catheter between the region of the aortic arch and the sharper distal curves such as the primary and secondary curves 32, 30 in a Judkins-left catheter. The most distal portion of the left anterior descending artery, on average, is about 15 centimeters from the left coronary ostium. The secondary curve of the guide catheter is approximately three to six centimeters from the distal tip of the guide catheter. Similarly, the length of the intermediate section 46 is such that even if the guidewire is advanced fully into the left anterior descending artery, the juncture of the proximal shaft 50, at connector tube 52, with the intermediate shaft 58 will remain proximally to the portion of the guide catheter that resides in the region of the aortic arch 16. It should be understood that it may be desirable to make and use guidewires having shorter distal sections, as described above, for example, when it is not necessary to reach into the most distal extremities of the coronary arteries.

From the foregoing it will be appreciated that the invention provides a small diameter steerable guidewire adapted for use in percutaneous transluminal coronary angioplasty in which the guidewire is formed with distinct segments each adapted to maximize the performance characteristics of each segment of the guidewire in its respective range of cardiovascular anatomy. The guidewire is essentially kink free while retaining a high degree of pushability and rotational transmission from the proximal to the distal end. Moreover, the guidewire is considered to achieve such maximum performance while providing improved tactile response for the physician.

It should be understood that the foregoing description, particularly with reference to the illustrative diameters, has been based on a guidewire having a nominal diameter of 0.010 inches. The invention, however, relates to the full range of guidewire diameters conventionally used in percutaneous transluminal coronary angioplasty, typically in the range of 0.010 inches to 0.018 inches and may be effective as a steerable guidewire even in smaller diameters, such as 0.009 inches.

It also should be understood that the foregoing description of the invention is intended merely to be illustrative thereof and that other embodiments, modifications and equivalents may be apparent to those skilled in the art without departing from the scope of the invention.

Having thus described the invention what I desire to claim and secure by Letters Patent is:

1. A small diameter steerable PTCA guidewire comprising:
   an elongate flexible shaft having a proximal section, an intermediate section connected to the proximal section and a distal section connected to the intermediate section;
   the distal section being more flexible than the intermediate section;
   the intermediate section being more flexible than the proximal section;
   the distal section being approximately fifteen to thirty centimeters in length;
   the intermediate section being approximately twelve to eighteen centimeters in length whereby the intermediate section may extend through the region of a human aortic arch when the distal section is disposed, at least in part, in a coronary artery;
   the proximal section being formed from a material different from that of the intermediate and distal sections and has a modulus of elasticity that is substantially greater than about 30 million p.s.i., the intermediate and distal sections being formed from a material having a modulus of elasticity substantially less than that of the material from which the proximal section is formed;
   said shaft being not substantially greater in diameter than about 0.018 inches;
   said shaft being sufficiently torsionally rigid along its length so that when the intermediate section is in a configuration corresponding to that of a human aortic arch and with the distal segment having at least one bend of a shorter radius than that of a human aortic arch, the shaft is capable of transmitting controllably from its proximal to its distal end rotation applied at the proximal end.

2. A small diameter steerable PTCA guidewire as defined in claim 1 further comprising:
   an elongate flexible tubular member extending over the distal section of the shaft, the tubular member being attached at its proximal end to the region of the juncture between the intermediate and distal sections; and
   a smooth bead at the distal tip of the tubular member.

3. A small diameter steerable PTCA guidewire as defined in claim 2 further comprising:
   an elongate malleable wire connected at one end to the distal tip of the shaft and at its other end to the tip bead.

4. A small diameter steerable PTCA guidewire as defined in any one of claims 1–3 wherein the intermediate and distal sections of the shaft are formed from a metal having pseudo-elastic properties at body temperatures.

5. A small diameter steerable PTCA guidewire as defined in claim 4 wherein said pseudo-elastic material comprises nitinol.

6. A small diameter steerable PTCA guidewire as defined in claim 5 wherein said nitinol comprises an alloy of 55% nickel (by weight) and 45% titanium.

7. A small diameter steerable PTCA guidewire as defined in claim 4 wherein the material of a proximal section is not pseudo-elastic.

8. A small diameter steerable PTCA guidewire as defined in claim 2 wherein the elongate flexible tubular member comprises a helical coil.

9. A small diameter steerable PTCA guidewire as defined in claim 1 wherein the proximal section of the shaft is formed from an alloy of tungsten and rhenium.

10. A small diameter steerable PTCA guidewire as defined in claim 9 wherein said alloy is 97% tungsten by weight and 3% rhenium.

11. A small diameter steerable PTCA guidewire as defined in claim 1 wherein
   the intermediate section is formed from a material having a higher modulus of elasticity than the distal section.

12. A small diameter steerable PTCA guidewire as defined in claim 1 wherein said proximal section is substantially more torsionally rigid and has substantially greater column strength than the intermediate or distal sections.

13. A small diameter steerable PTCA guidewire for use with an over-the-wire PTCA catheter and a guide catheter adapted to receive the PTCA catheter and guidewire comprising, in combination:
   the guide catheter having a proximal portion adapted to be deployed in the aorta proximally of the aortic arch, an intermediate section adapted to pass through the aortic arch and a distal segment adapted to reside in the ascending portion of the aorta, the distal portion having at least one bend of a radius shorter than the radius assumed by the intermediate portion when the intermediate portion passes through the aortic arch;

the guidewire having an elongate flexible shaft having a proximal section, an intermediate section connected to the proximal section and a distal section connected to the intermediate section;

the distal section being more flexible than the intermediate section;

the intermediate section being more flexible than the proximal section whereby the intermediate section may extend through the region of a human aortic arch when the distal section is disposed, at least in part, in a coronary artery;

the proximal section being formed from a material different from that of the intermediate and distal sections and has a modulus of elasticity that is substantially greater than about 30 million p.s.i., the intermediate and distal sections being formed from a material having a modulus of elasticity substantially less than that of the material from which the proximal section is formed;

said shaft being not substantially greater in diameter than about 0.018 inches;

the lengths of the proximal intermediate and distal section of the guidewire being such that throughout the full range of lengthwise movement of the guidewire with respect to the guide catheter, the proximal section of the guidewire will remain in the proximal section of the guide catheter and the distal section of the guidewire will remain distally of the intermediate section of the guide catheter;

said guidewire shaft being sufficiently torsionally rigid along its length so that when the intermediate section of the guidewire is in a configuration corresponding to that of a human aortic arch and with the distal segment of the guidewire having at least one bend of a shorter radius than that of a human aortic arch, the shaft is capable of transmitting controllably from its proximal to its distal end rotation applied at the proximal end.

14. A small diameter steerable PTCA guidewire as defined in any one of claims 1 or 13 wherein the diameter of the shaft is about 0.010 inches.

15. A small diameter steerable guidewire as defined in any one of claims 1 or 13 further comprising:
the outer diameters of the proximal and intermediate sections of the shaft being substantially equal.

16. A small diameter steerable PTCA guidewire as defined in claim 1 further comprising:
the outer diameters of the proximal and intermediate sections being substantially the same.

17. A small diameter steerable PTCA guidewire as defined in claim 1 further comprising:
a thin coating about the external surface of the guidewire, the coating being not substantially thicker than that necessary for enhancement of the lubricity of the guidewire.

18. A small diameter steerable PTCA guidewire as defined in claim 16 further comprising:
a thin coating about the external surface of the guidewire, the coating being not substantially thicker than that necessary for enhancement of the lubricity of the guidewire.

19. A small diameter steerable PTCA guidewire comprising an elongate flexible shaft having a proximal section that comprises the major length of the shaft, said proximal section being formed from a material having a modulus of elasticity substantially greater than 30 million p.s.i.;
the portion of the shaft extending distally of the proximal section being formed from a material having a modulus of elasticity no greater than about 30 million p.s.i.

20. A guidewire as defined in claim 19 wherein the overall length of the guidewire is approximately 175 centimeters and the length of the proximal section is approximately 140 centimeters.

21. A guidewire as defined in either one of claims 19 or 20 wherein the modulus of elasticity of the proximal section is at least about 50 million p.s.i.

22. A method of directing a PTCA catheter into a selected coronary artery comprising:
providing an elongate flexible shaft having a proximal section, an intermediate section connected to the proximal section and a distal section connected to the intermediate section;

the distal section being more flexible than the intermediate section;

the intermediate section being more flexible than the proximal section whereby the intermediate section may extend through the region of a human aortic arch when the distal section is disposed, at least in part, in a coronary artery;

the proximal section being formed from a material different from that of the intermediate and distal sections and has a modulus of elasticity that is substantially greater than about 30 million p.s.i., the intermediate and distal sections being formed from a material having a modulus of elasticity substantially less than that of the material from which the proximal section is formed;

said shaft being not substantially greater in diameter than about 0.018 inches;

said shaft being sufficiently torsionally rigid along its length so that when the intermediate section is in a configuration corresponding to that of a human aortic arch and with the distal segment having at least one bend of a shorter radius than that of a human aortic arch, the shaft is capable of transmitting controllably from its proximal to its distal end rotation applied at the proximal end;

said method further comprising placing said guidewire in a patient's aorta and advancing the guidewire distally through the aortic arch and into the coronary arterial tree;

manipulating the guidewire by combined rotational and translational movement; and maintaining the proximal section of the guidewire shaft proximally of the aortic arch and the distal section of the shaft distally of the aortic arch at all times during said manipulation of the guidewire.

23. A small diameter steerable PTCA guidewire comprising:
an elongate flexible shaft having a proximal section, an intermediate section connected to the proximal section and a distal section connected to the intermediate section;

the distal section being more flexible than the intermediate section;

the intermediate section being more flexible than the proximal section;

the distal section being approximately fifteen to thirty centimeters in length;

the intermediate section being approximately twelve to eighteen centimeters in length whereby the intermediate section may extend through the region of a human aortic arch when the distal section is disposed, at least in part, in a coronary artery;

the proximal section being formed from a material having different characteristics from that of the intermediate and distal sections and has a modulus of elasticity that is substantially greater than about 30 million p.s.i., the intermediate and distal sections being formed from a material having a modulus of elasticity substantially less than that of the material from which the proximal section is formed;

said shaft being not substantially greater in diameter than about 0.018 inches;

said shaft being sufficiently torsionally rigid along its length so that when the intermediate section is in a configuration corresponding to that of a human aortic arch and with the distal segment having at least one bend of a shorter radius than that of a human aortic arch, the shaft is capable of transmitting controllably from its proximal to its distal end rotation applied at the proximal end.

24. A small diameter steerable PTCA guidewire as defined in claim 23 further comprising:

the outer diameters of the proximal and intermediate sections being substantially the same.

25. A small diameter steerable PTCA guidewire as defined in claim 23 further comprising:

a thin coating about the external surface of the guidewire, the coating being not substantially thicker than that necessary for enhancement of the lubricity of the guidewire.

26. A small diameter steerable PTCA guidewire as defined in claim 24 further comprising:

a thin coating about the external surface of the guidewire, the coating being not substantially thicker than that necessary for enhancement of the lubricity of the guidewire.

* * * * *

UNITED STATES PATENT AND TRADEMARK OFFICE
CERTIFICATE OF CORRECTION

PATENT NO. : 5,365,943
DATED : November 22, 1994
INVENTOR(S) : Lex P. Jansen

It is certified that error appears in the above-indentified patent and that said Letters Patent is hereby corrected as shown below:

Title page, item [75] "Londonberry, N.H." should read --Londonderry, N.H.--.

In the Abstract, last line, change "guidewire" to --guide catheter--.

Col. 7, line 58, change "Locktire" to --Loctite---; line 59, change "Locktite" to --Loctite--.

Signed and Sealed this

Sixteenth Day of July, 1996

Attest:

BRUCE LEHMAN

Attesting Officer

Commissioner of Patents and Trademarks